US012661020B2

(12) United States Patent
   Bavry

(10) Patent No.: US 12,661,020 B2
(45) Date of Patent: Jun. 23, 2026

(54) SYSTEMS, METHODS, AND DEVICES FOR CARDIAC PROCEDURES WITH A MULTI-PRESSURE MEASUREMENT CATHETER

(71) Applicant: THE BOARD OF REGENTS OF THE UNIVERSITY OF TEXAS SYSTEM, Austin, TX (US)

(72) Inventor: Anthony Alexander Bavry, Dallas, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 18/840,999

(22) PCT Filed: Feb. 22, 2023

(86) PCT No.: PCT/US2023/063047
   § 371 (c)(1),
   (2) Date: Aug. 23, 2024

(87) PCT Pub. No.: WO2023/164491
   PCT Pub. Date: Aug. 31, 2023

(65) Prior Publication Data
   US 2025/0160664 A1     May 22, 2025

Related U.S. Application Data

(60) Provisional application No. 63/313,700, filed on Feb. 24, 2022.

(51) Int. Cl.
   *A61B 5/00*       (2006.01)
   *A61B 5/0215*     (2006.01)
   (Continued)

(52) U.S. Cl.
   CPC ........ *A61B 5/02158* (2013.01); *A61B 5/6852* (2013.01); *A61M 31/005* (2013.01);
   (Continued)

(58) Field of Classification Search
   CPC .................................................. A61B 5/02158
   See application file for complete search history.

(56) References Cited

U.S. PATENT DOCUMENTS

| | | |
|---|---|---|
| 4,777,951 A | 10/1988 | Cribier et al. |
| 8,613,706 B2 | 12/2013 | Langston |
| | (Continued) | |

OTHER PUBLICATIONS

Patent Cooperation Treaty, International Search Report and Written Opinion, International Application No. PCT/US23/63047, date of mailing Aug. 29, 2023, 9 pages.
(Continued)

*Primary Examiner* — Joseph M Santos Rodriguez
(74) *Attorney, Agent, or Firm* — Polsinelli PC

(57)          ABSTRACT

Systems, methods, and devices for performing heart procedures include a multi-functional catheter with a multi-lumen arrangement. The multi-lumen arrangement includes a central lumen formed by an inner tube with multiple pressure channels embedded in the wall of the catheter. The central lumen has a first end hole terminating at a distal end of the multi-functional catheter. The outer lumen has one or more second side holes. Moreover, a welded tip can maintain a consistent diameter for the distal end. Multiple radiopaque markers can identify various portions of multi-functional catheter to aid in positioning the lumens at different placements in the heart and/or crossing the aortic valve. Accordingly, multiple diagnostic procedures can be performed with the multi-functional catheter, such as a coronary angiogram and a trans-valvular pressure gradient measurement, while omitting reliance on additional catheters or a digital console system.

20 Claims, 10 Drawing Sheets

(51) Int. Cl.
    *A61M 31/00*         (2006.01)
    *A61M 25/00*         (2006.01)
    *A61M 25/09*         (2006.01)

(52) U.S. Cl.
    CPC . *A61M 2025/0003* (2013.01); *A61M 25/0032*
       (2013.01); *A61M 2025/0039* (2013.01); *A61M*
                               *25/09* (2013.01)

(56)                  References Cited

U.S. PATENT DOCUMENTS

| 2005/0203434 A1 | 9/2005 | Kassab |
| 2014/0243688 A1 | 8/2014 | Caron et al. |

OTHER PUBLICATIONS

Dec. 18, 2025—(EP) Extended European Search Report—App 23760880.7, 13 Pages.

SYSTEMS, METHODS, AND DEVICES FOR CARDIAC PROCEDURES WITH A MULTI-PRESSURE MEASUREMENT CATHETER

CROSS-REFERENCE TO RELATED APPLICATION

This application claims priority to U.S. Provisional Patent Application No. 63/313,700, filed Feb. 24, 2022 and titled "SYSTEMS, METHODS, AND DEVICES FOR CARDIAC DIAGNOSTICS WITH A DUAL LUMEN CATHETER," which is incorporated herein by reference in its entirety.

BACKGROUND

1. Field

The present disclosure relates generally to devices for performing cardiac diagnostics. In at least one example, the present disclosure relates to a system including a catheter for trans-valvular pressure measurements.

2. Discussion of Related Art

In approximately half of the cases of symptomatic aortic stenosis (i.e., aortic valve narrowing), there is ambiguity regarding the severity of the valve condition. In such cases, precise diagnosis requires direct trans-valvular pressure measurement by invasive cardiac catheterization. This involves measuring the pressure proximal and distal to the aortic valve simultaneously. Some devices can obtain pressure measurements. However, such devices can require extra steps with an initial separate catheter/wire to advance across the aortic valve. Other devices, such as the Millar solid state catheter, are large and require a significant capital investment to purchase the digital console and catheters, making this device less preferential for clinical use. Furthermore, these larger and more complex catheters often have difficulty advancing across the aortic valve, and so additional wires and steering catheters are typically used first to get the intended catheter across the aortic valve.

In current practice, there are several 'work-arounds' to obtain simultaneous trans-aortic pressure measurements, for instance, by performing an additional arterial puncture to be used for a separate catheter. However, the measurements obtained from these techniques can be imprecise and create additional safety concerns because creating an extra arterial puncture increases the risk of bleeding and vascular injury.

It is with these observations in mind, among others, that various aspects of the present disclosure were conceived and developed.

BRIEF SUMMARY

The presently disclosed technology addresses the foregoing problems by providing a multi-functional diagnostic catheter. The—functional diagnostic catheter can include a catheter with a pressure measurement arrangement operable to perform a coronary angiogram, cross an aortic valve, and measure a trans-valvular gradient. The pressure measurement arrangement can include a central pressure measurement pathway disposed at least partly within the catheter, the central pressure measurement pathway terminating at a first hub to connect an end hole of the central pressure measurement pathway to a pressure transducer, and/or an outer pressure measurement pathway having a first portion disposed within the catheter and a second portion disposed outside the catheter, the second portion terminating at a second hub to connect a side hole of the outer pressure measurement pathway to the pressure transducer, the side hole being located at a side of the catheter spaced a defined distance from an end of the catheter.

In some examples, the outer pressure measurement pathway is a pressure channel disposed in an interior material forming the central pressure measurement pathway. The distal tip can have a first inner diameter greater than an inner diameter of the central pressure measurement pathway. Additionally, the distal tip can be formed of a soft material. The defined distance can be a first defined distance, and/or the catheter can include a first radiopaque marker at the end hole of the central pressure measurement pathway and a second radiopaque marker circumferentially around the side of the catheter a second defined distance from the first radiopaque marker.

In some scenarios, the pressure measurement arrangement is operable to measure a left ventricular pressure using the end hole of the central pressure measurement pathway while measuring an aortic pressure using the side hole of the outer pressure measurement pathway. Measuring the left ventricular pressure and the aortic pressure can use two analog signals generated by two pressure transducers while omitting reliance on a digital-based pressure sensor console system. Also, the central pressure measurement pathway can be operable to receive a guidewire for crossing an aortic valve, and/or the guidewire can be removable from the central pressure measurement pathway while maintaining the central pressure measurement pathway in a left ventricular once the aortic valve is crossed. Additionally or alternatively, the central pressure measurement pathway is operable to inject a contrast dye prior to crossing an aortic valve to perform selective coronary angiogram. Moreover, a first portion of the multi-functional diagnostic catheter, including the central pressure measurement pathway with the outer pressure measurement pathway, can have a first inner diameter; and/or a second portion of the multi-functional diagnostic catheter, including the central pressure measurement pathway and omitting the outer pressure measurement pathway, can have a second inner diameter greater than the first inner diameter In some examples, a multi-functional diagnostic catheter can include a catheter with a multi-pressure channel arrangement operable to perform a coronary angiogram, cross an aortic valve, and measure a trans-valvular gradient. The multi-pressure channel arrangement can include a central pressure measurement pathway disposed at least partly within the catheter. The central pressure measurement pathway can terminate at a first hub to connect a distal end hole of the central pressure measurement pathway to one or more pressure transducers; and/or one or more outer pressure measurement pathways formed into a sidewall material of the central pressure measurement pathway. The one or more outer pressure measurement pathways can terminate at a second hub to connect one or more side holes of the one or more outer pressure measurement pathways to the one or more pressure transducers, the one or more side holes being located at a side of the catheter spaced one or more defined distances from an end of the catheter.

In some scenarios, the one or more side holes include at least three side holes in a staggered arrangement around the catheter. Furthermore, the one or more outer pressure measurement pathways can include at least three elongated ellipse channels. The multi-functional diagnostic catheter can be a 7 French (7Fr) catheter or a 6 French (6Fr) catheter. The multi-functional diagnostic catheter can further include a first inner diameter at a mid-shaft portion of the multi-functional diagnostic catheter which extends form a proximal portion of the multi-functional diagnostic catheter to a near-distal portion of the multi-functional diagnostic catheter; and/or a second inner diameter at a distal portion of the multi-functional diagnostic catheter, the second inner diameter being greater than the first inner diameter. By way of example, the central pressure measurement pathway can be operable to cross a stenotic aortic valve using a guidewire disposed within the central pressure measurement pathway. Furthermore, the multi-functional diagnostic catheter can be operable to measure a left ventricular pressure using the distal end hole of the central pressure measurement pathway while measuring an aortic pressure using the one or more side holes of the one or more outer pressure measurement pathways upon crossing the stenotic aortic valve with the guidewire.

In some instances, a method to perform multiple diagnostic functions using a catheter with a multi-pressure measurement pathway arrangement can include measuring a left ventricular pressure with an end hole of a central pressure measurement pathway. The central pressure measurement pathway can be at least partly disposed within the catheter and terminating at a first hub to connect the end hole of the central pressure measurement pathway to a pressure transducer, and the end hole of the central pressure measurement pathway can be located at a distal end of the catheter. The method can also include measuring an aortic pressure with one or more end holes of one or more outer pressure measurement pathway, the one or more outer pressure measurement pathway disposed in the catheter and terminating at a second hub to connect one or more end holes of the one or more outer pressure measurement pathway to a pressure transducer, the one or more end holes being located along an outer sidewall of the catheter spaced one or more defined distances from the end hole of the central pressure measurement pathway.

In some scenarios, measuring the left ventricular pressure and the aortic pressure is performed with three or more side holes to measure a trans-valvular gradient while omitting reliance on a pressure sensor console system. The method can further include making an initial crossing of an aortic valve with the central pressure measurement pathway using a guidewire disposed within the central pressure measurement pathway. Furthermore, the method can include injecting a contrast dye into coronary arteries using the central pressure measurement pathway before or after measuring a trans-valvular gradient with the central pressure measurement pathway and three or more outer pressure measurement pathway.

The foregoing is intended to be illustrative and is not meant in a limiting sense. Many features of the embodiments may be employed with or without reference to other features of any of the embodiments. Additional aspects, advantages, and/or utilities of the presently disclosed technology will be set forth in part in the description that follows and, in part, will be apparent from the description, or may be learned by practice of the presently disclosed technology.

BRIEF DESCRIPTION OF THE DRAWINGS

The foregoing summary, as well as the following detailed description, will be better understood when read in conjunction with the appended drawings. For the purpose of illustration, there is shown in the drawings certain embodiments

Figure 1:
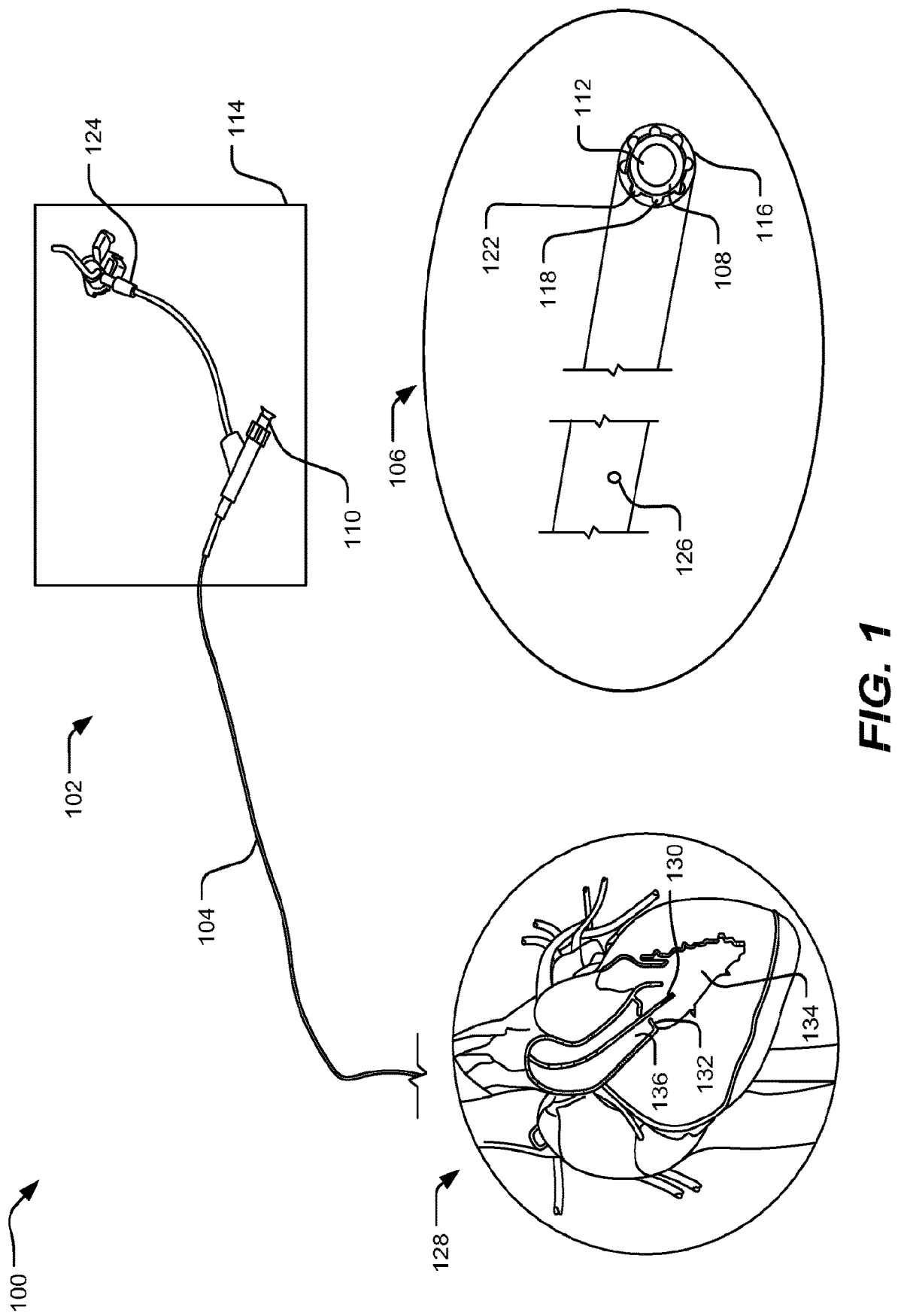
Figure 2:
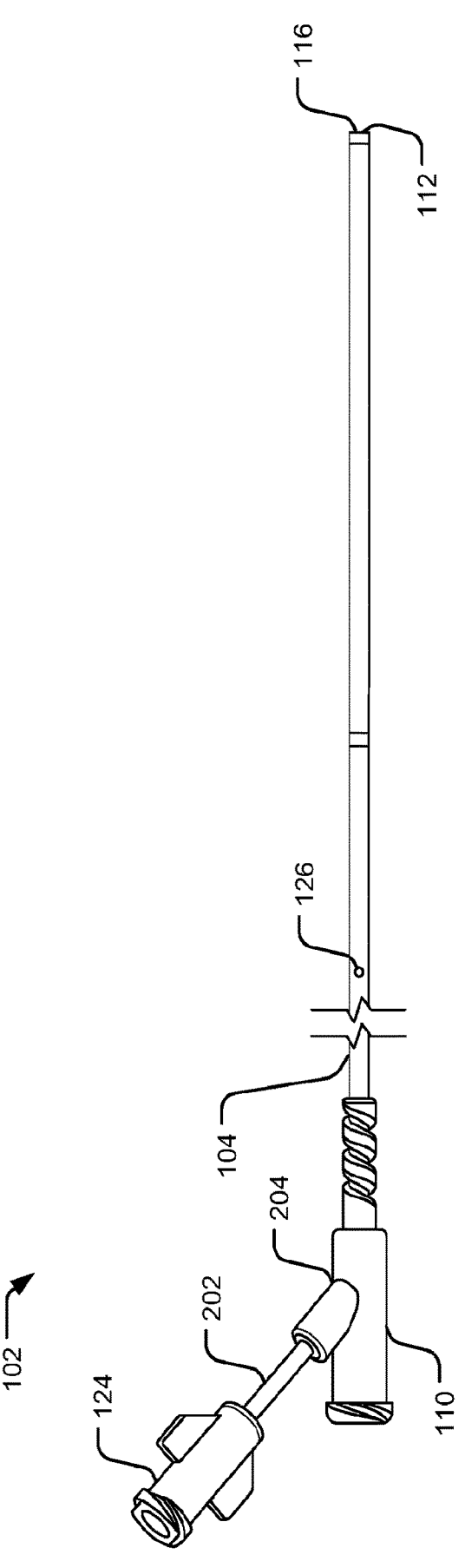
Figure 3:
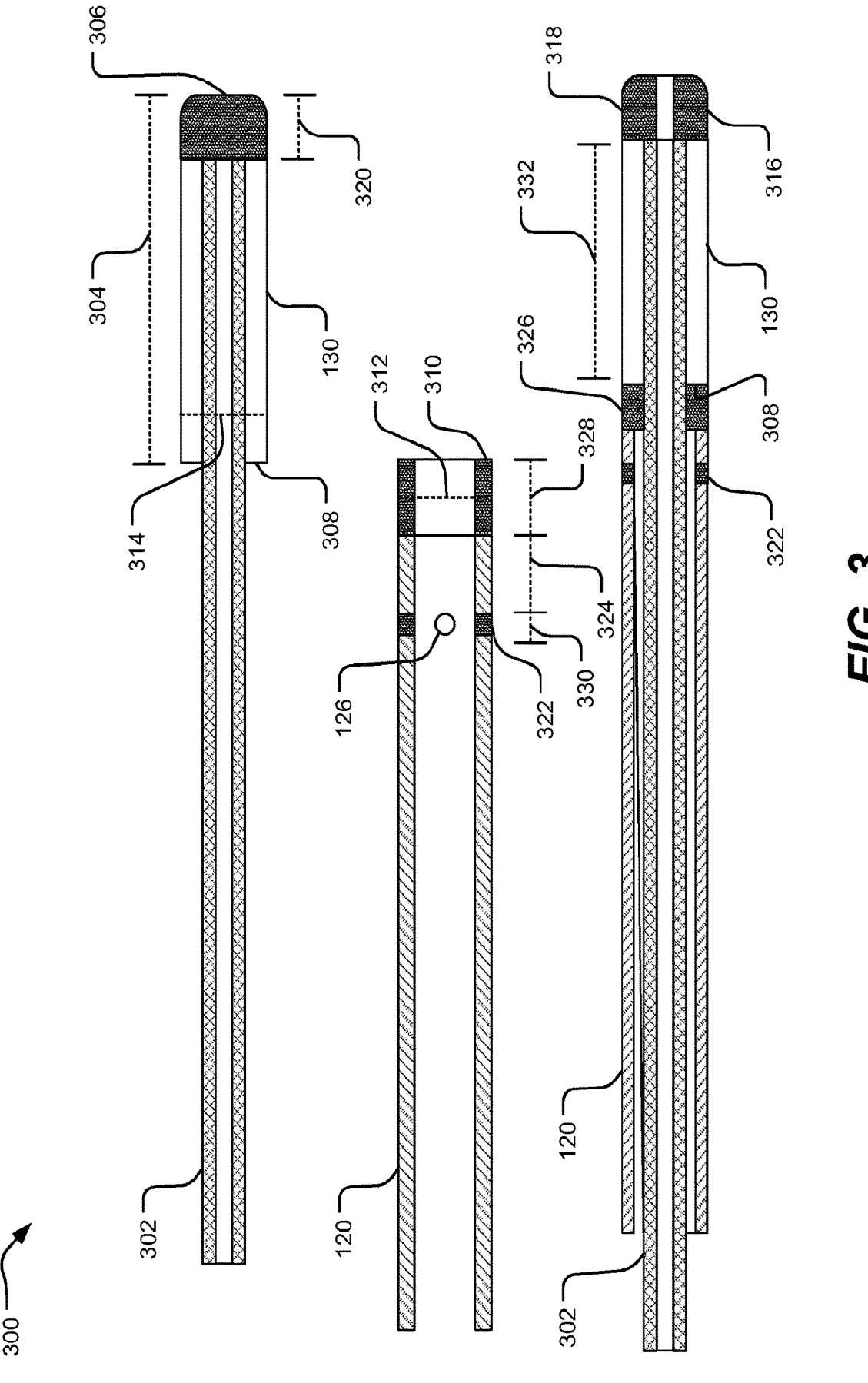
Figure 4:
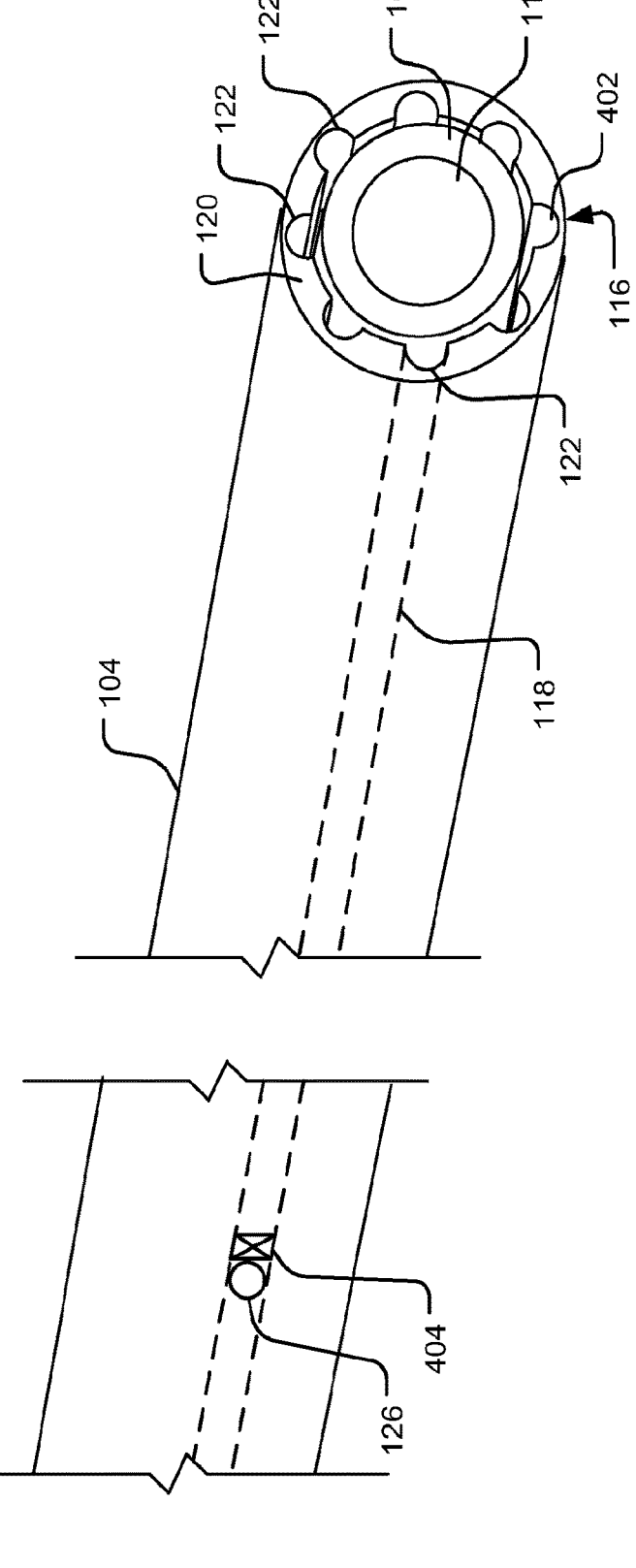
Figure 5:
Figure 5:
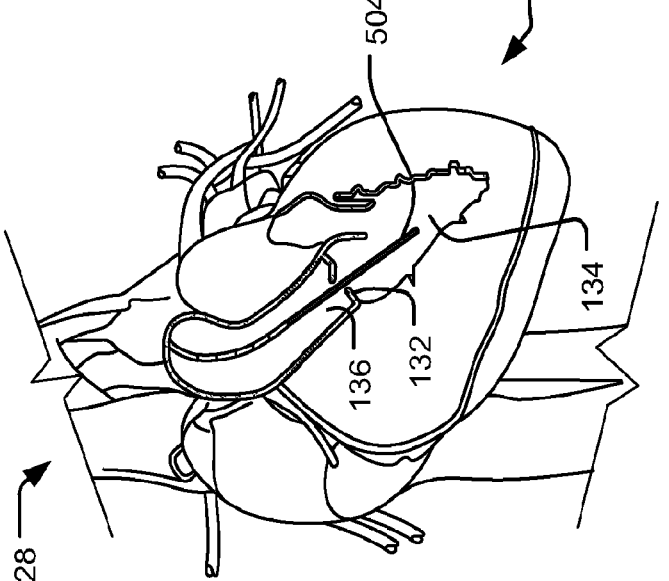
Figure 6:
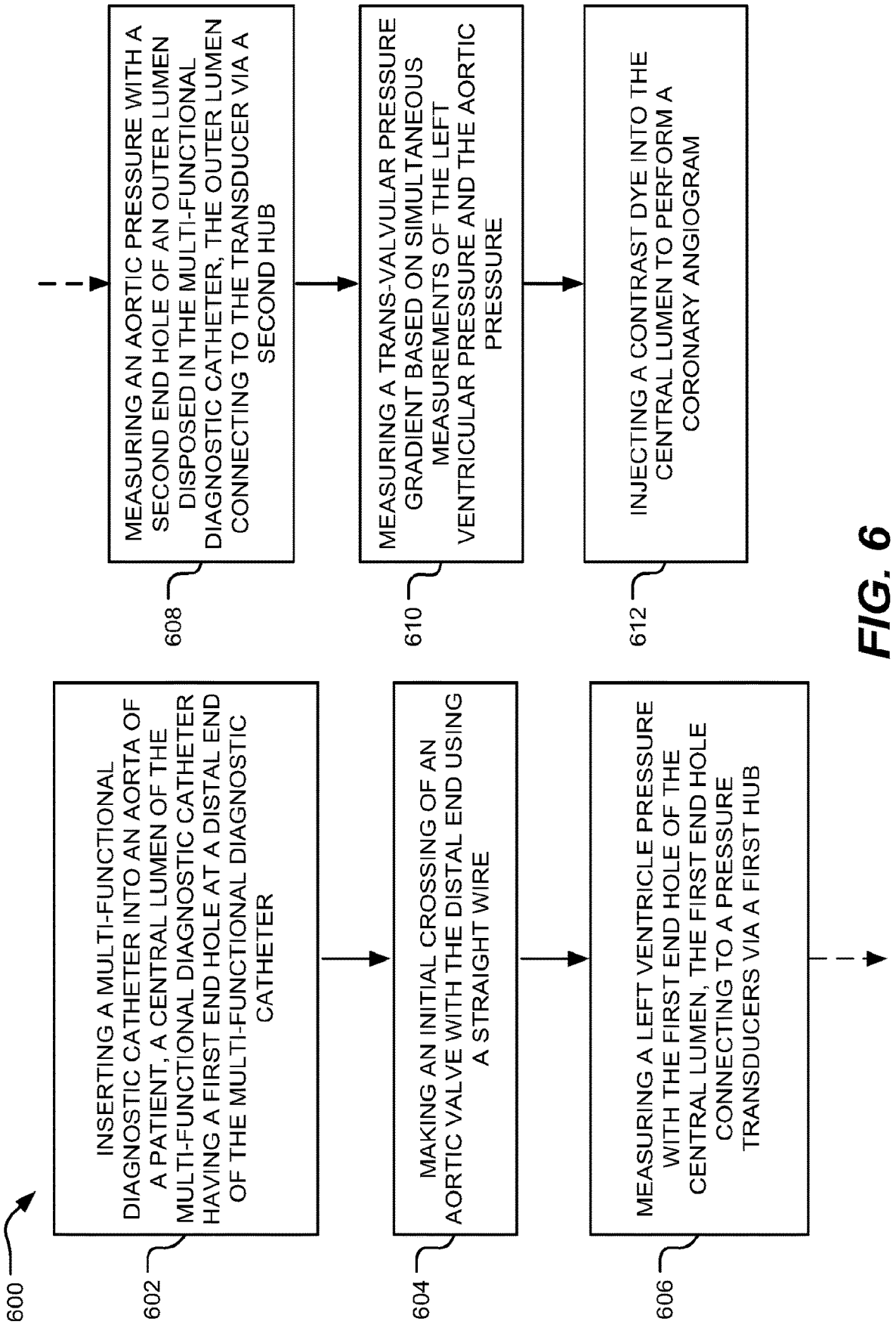
Figure 7A:
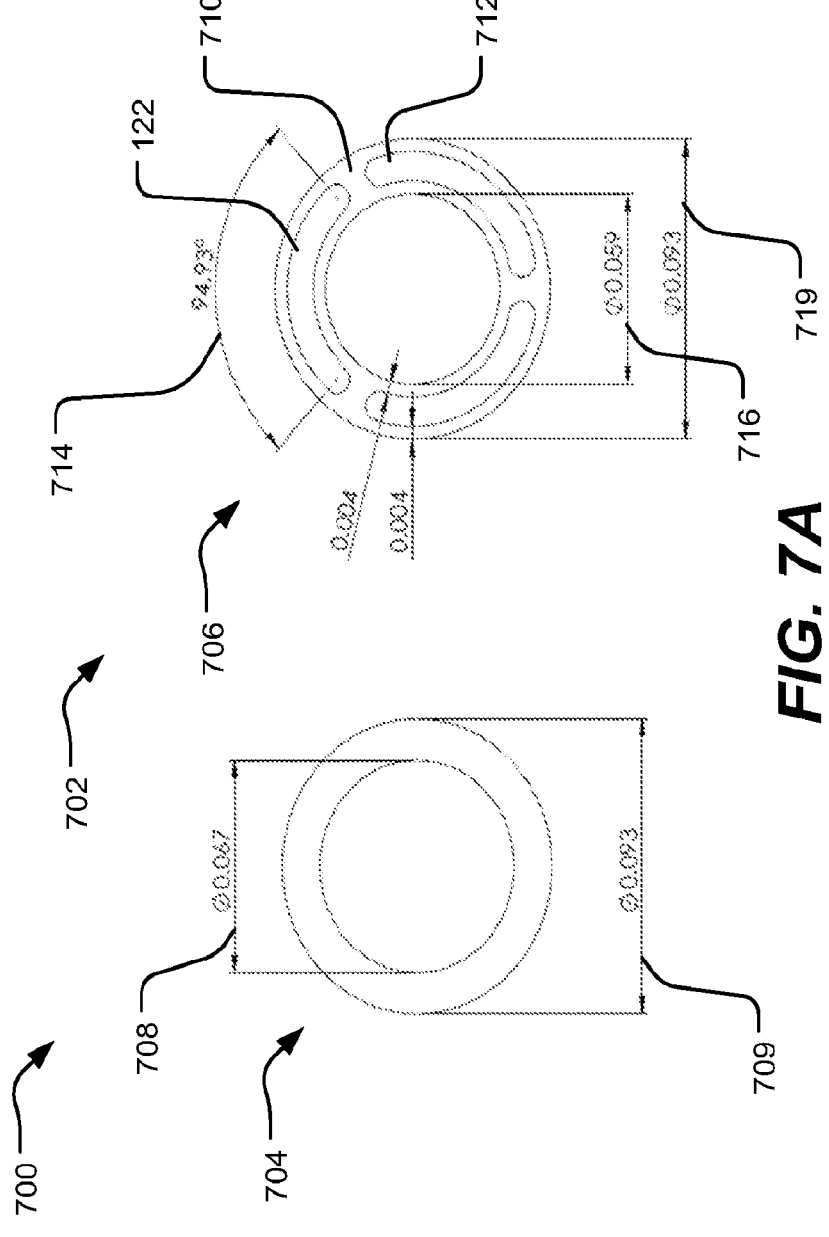
Figure 7B:
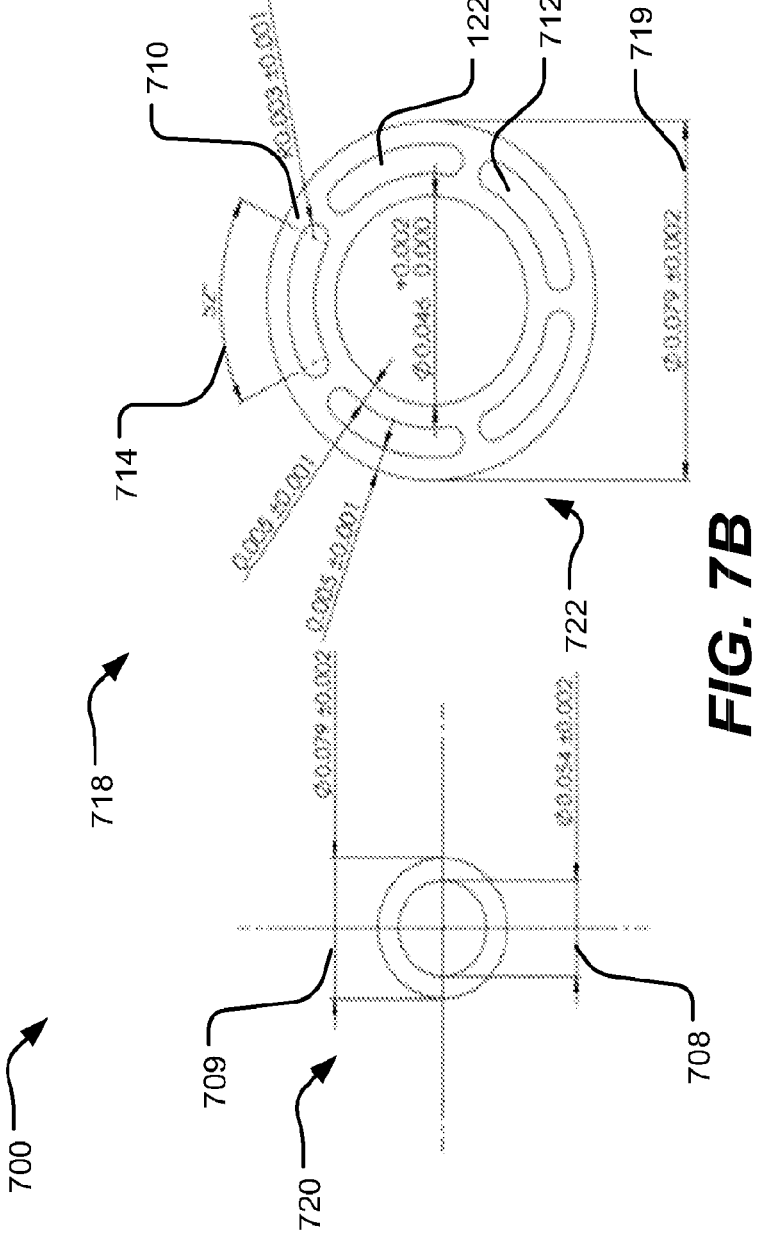
Figure 8:
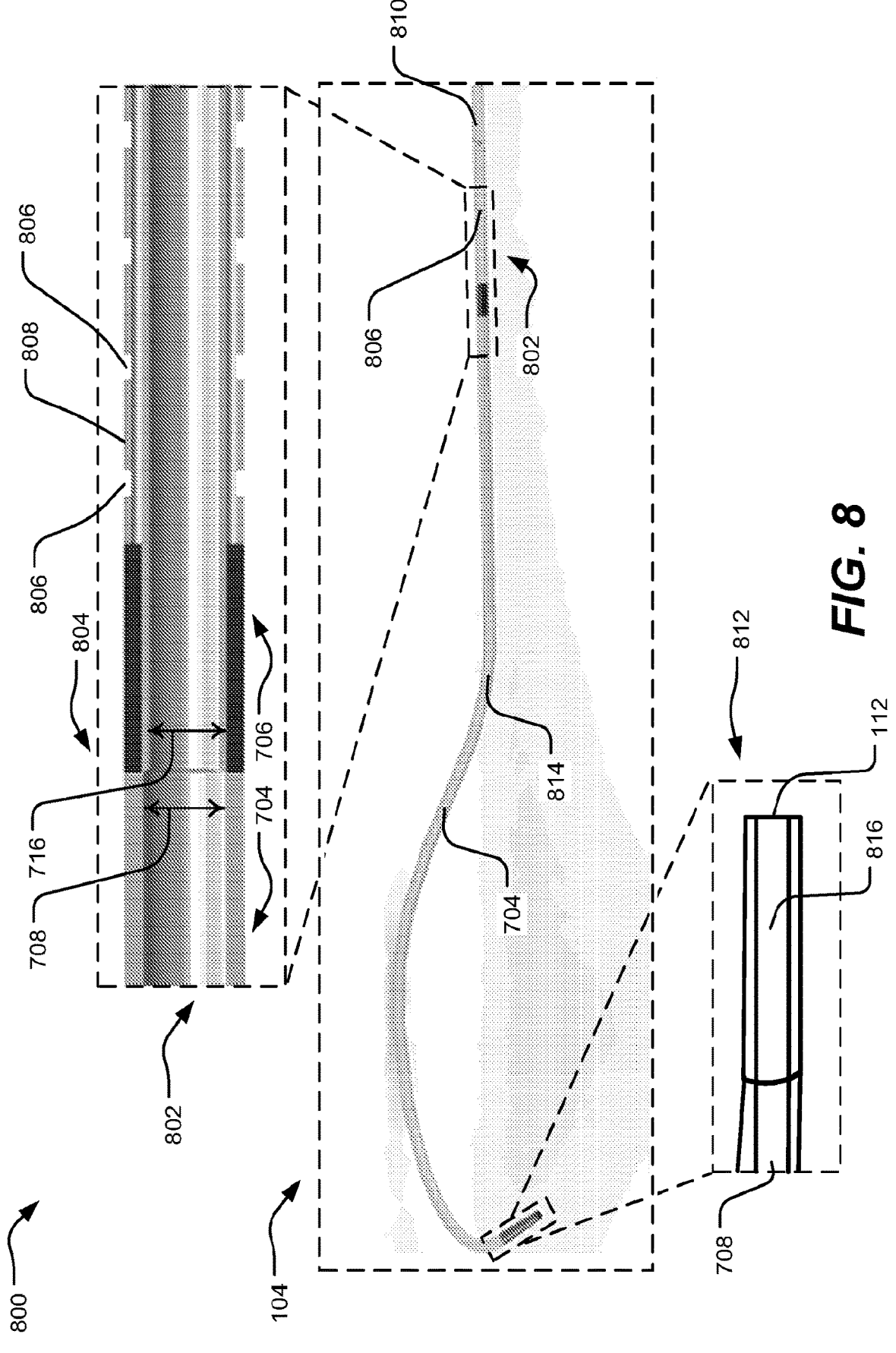
Figure 9:
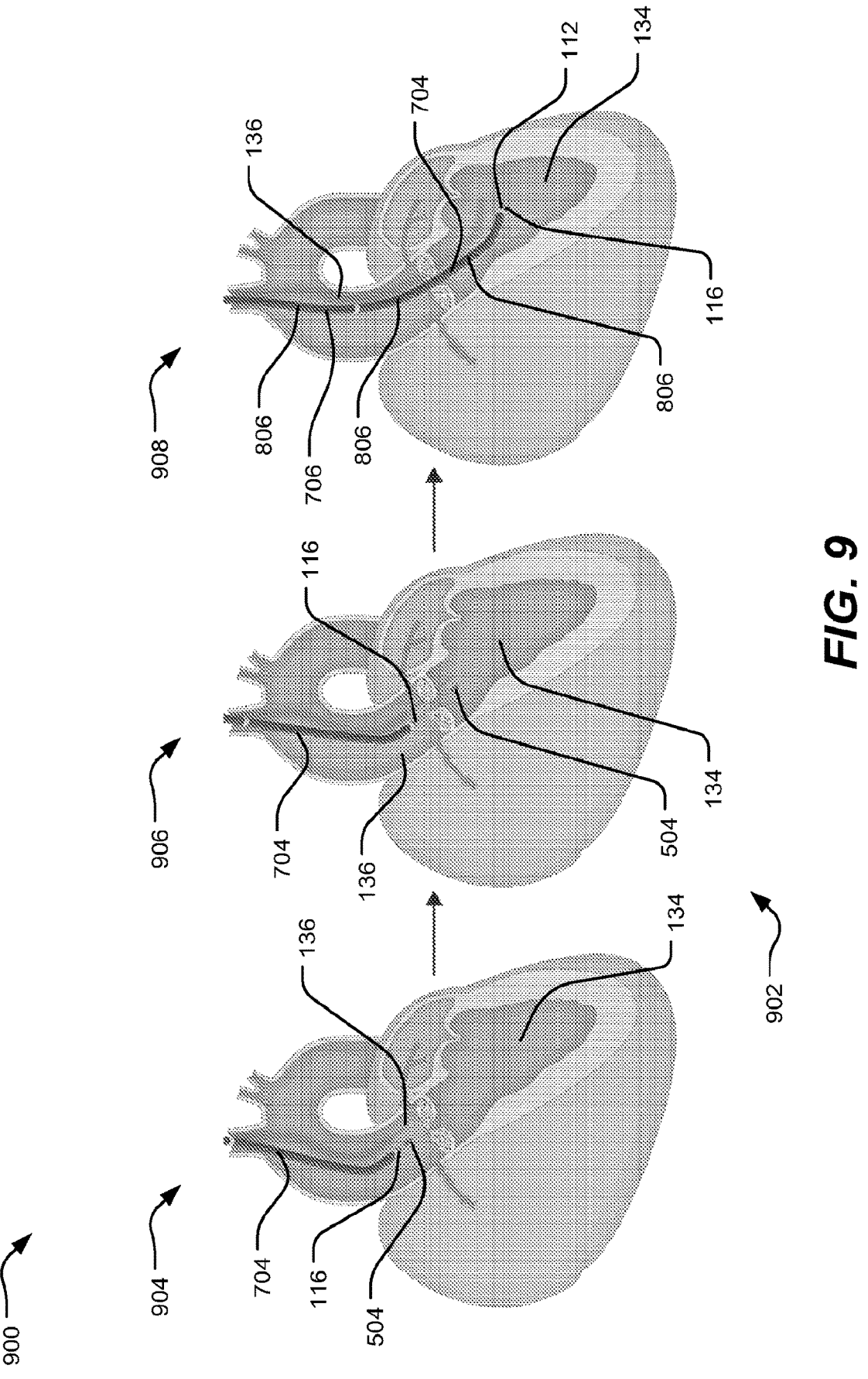

4 of the disclosed subject matter. It should be understood, however, that the disclosed subject matter is not limited to the precise embodiments and features shown. The accompanying drawings, which are incorporated in and constitute a part of this specification, illustrate an implementation of systems and methods consistent with the disclosed subject matter and, together with the description, serves to explain advantages and principles consistent with the disclosed subject matter, in which:

FIG. 1 illustrates an example system for performing cardiac procedures using a multi-functional catheter;

FIG. 2 illustrates an example system for performing cardiac procedures using a multi-functional catheter with a first hub and a second hub, which can form at least a portion of the system depicted in FIG. 1;

FIG. 3 illustrates an example system for performing cardiac procedures using a multi-functional catheter with a welded tip and radiopaque markers, which can form at least a portion of the system depicted in FIG. 1;

FIG. 4 illustrates an example system for performing cardiac procedures using a multi-functional catheter with a central lumen and an outer lumen, which can form at least a portion of the system depicted in FIG. 1;

FIG. 5 illustrates an example system for performing cardiac procedures using a multi-functional catheter with a guidewire for crossing an aortic valve, which can form at least a portion of the system depicted in FIG. 1;

FIG. 6 illustrates an example method for performing cardiac procedures using a multi-functional catheter with a multi-lumen arrangement, which can be performed by at least the system depicted in FIG. 1;

FIG. 7A illustrates an example system for performing cardiac procedures using a multi-functional catheter with a multi-lumen arrangement, which can form at least a portion of the system depicted in FIG. 1;

FIG. 7B illustrates an example system for performing cardiac procedures using a multi-functional catheter with a multi-pressure channel arrangement, which can form at least a portion of the system depicted in FIG. 1;

FIG. 8 illustrates an example system for performing cardiac procedures using a multi-functional catheter with a distal portion, a mid-shaft portion, and a tapered tip, which can form at least a portion of the system depicted in FIG. 1; and FIG. 9 illustrates example system(s) and method(s) for performing a heart entry procedure, cardiac diagnostics, and/or cardiac treatment using a multi-functional catheter with a guidewire for crossing an aortic valve, which can be performed by at least the system depicted in FIG. 1.

DETAILED DESCRIPTION

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts may be exaggerated to better illustrate details and features of the present disclosure.

I. Terminology

The phraseology and terminology employed herein are for the purpose of description and should not be regarded as limiting. For example, the use of a singular term, such as, "a" is not intended as limiting of the number of items. Also, the use of relational terms such as, but not limited to, "top," "bottom," "left," "right," "upper," "lower," "down," "up," and "side," are used in the description for clarity in specific reference to the figures and are not intended to limit the scope of the presently disclosed technology or the appended claims. Further, it should be understood that any one of the features of the presently disclosed technology may be used separately or in combination with other features. Other systems, methods, features, and advantages of the presently disclosed technology will be, or become, apparent to one with skill in the art upon examination of the figures and the detailed description. It is intended that all such additional systems, methods, features, and advantages be included within this description, be within the scope of the presently disclosed technology, and be protected by the accompanying claims.

Further, as the presently disclosed technology is susceptible to embodiments of many different forms, it is intended that the present disclosure be considered as an example of the principles of the presently disclosed technology and not intended to limit the presently disclosed technology to the specific embodiments shown and described. Any one of the features of the presently disclosed technology may be used separately or in combination with any other feature. References to the terms "embodiment," "embodiments," and/or the like in the description mean that the feature and/or features being referred to are included in, at least, one aspect of the description. Separate references to the terms "embodiment," "embodiments," and/or the like in the description do not necessarily refer to the same embodiment and are also not mutually exclusive unless so stated and/or except as will be readily apparent to those skilled in the art from the description. For example, a feature, structure, process, step, action, or the like described in one embodiment may also be included in other embodiments but is not necessarily included. Thus, the presently disclosed technology may include a variety of combinations and/or integrations of the embodiments described herein. Additionally, all aspects of the present disclosure, as described herein, are not essential for its practice. Likewise, other systems, methods, features, and advantages of the presently disclosed technology will be, or become, apparent to one with skill in the art upon examination of the figures and the description. It is intended that all such additional systems, methods, features, and advantages be included within this description, be within the scope of the presently disclosed technology, and be encompassed by the claims.

Any term of degree such as, but not limited to, "substantially," as used in the description and the appended claims, should be understood to include an exact, or a similar, but not exact configuration. For example, "a substantially planar surface" means having an exact planar surface or a similar, but not exact planar surface. Similarly, the terms "about" or "approximately," as used in the description and the appended claims, should be understood to include the recited values or a value that is three times greater or one third of the recited values. For example, about 3 mm includes all values from 1 mm to 9 mm, and approximately 50 degrees includes all values from 16.6 degrees to 150 degrees.

The term "coupled" is defined as connected, whether directly or indirectly through intervening components, and is not necessarily limited to physical connections. The connection can be such that the objects are permanently connected or releasably connected. The terms "comprising," "including" and "having" are used interchangeably in this disclosure. The terms "comprising," "including" and "having" mean to include, but not necessarily be limited to the things so described. The term "real-time" or "real time" means substantially instantaneously.

Lastly, the terms "or" and "and/or," as used herein, are to be interpreted as inclusive or meaning any one or any combination. Therefore, "A, B, or C" or "A, B, and/or C" mean any of the following: "A," "B," or "C"; "A and B"; "A and C"; "B and C"; "A, B and C." An exception to this definition will occur only when a combination of elements, functions, steps or acts are in some way inherently mutually exclusive.

II. General Architecture

The systems disclosed herein improve upon previous techniques by providing a multi-functional catheter with a dual lumen arrangement. The dual lumen arrangement makes the multi-functional catheter a cost-effective, easy-to-use, and reliable device for crossing the aortic valve and measuring a trans-valvular pressure gradient. Moreover, the multi-functional catheter can incorporate a selective coronary injection procedure into the current workflow for cardiac catheterization. Some examples of the multi-functional catheter disclosed herein do not require a high-pressure system, obviating the design issue that can create a safety concern with previous catheter designs. Furthermore, unlike the Langston catheter—which requires initial valve crossing with another catheter, then exchanging for the Langston catheter—the multi-functional catheter is operable to facilitate crossing the aortic valve, even if the aortic valve is narrowed (e.g., stenotic). Furthermore, unlike the Millar catheter, some examples of the multi-functional catheter disclosed herein do not require purchase of a digital console for hemodynamic assessment. Rather, a more simplified and more efficient approach makes use of analog pressure signals measured by a pressure transducer.

In some instances, the multi-functional catheter includes one or more pressure measurement pathways to provide pressure readings to a transducer in addition to those provided by a central pressure pathway. For instance, a dual-lumen or multi-lumen arrangement of the multi-functional catheter includes a central lumen formed by an inner lumen and outer lumen formed by an exterior. The central lumen has a first end hole terminating at a distal end of the multi-functional catheter, which is connected to one or more pressure transducers via a first hub. The outer lumen has a second end hole as a side hole. For instance, a lumen channel can be formed into an inner surface of the exterior tube to define the outer lumen along a length of the multi-functional catheter and terminating at a side of the catheter. Once the distal end crosses the aortic valve, the first end hole is positioned in the left ventricular and the second end hole is positioned in the aorta. Accordingly, the trans-valvular pressure gradient can be measured by determining, with the one or more pressure transducers, a first pressure value corresponding to an aorta pressure and a second pressure value corresponding to a left ventricular pressure.

Moreover, a welded tip can be coupled to and/or define the distal end of the multi-functional catheter to maintain a consistent diameter for the distal end. The welded tip can be a rigid material which, along with the consistent diameter, improves the ability to navigate the distal end through the aortic valve and/or achieved desired positioning. Multiple radiopaque markers can identify various portions of multi-functional catheter to further aid in positioning the lumen end holes at different locations in the heart and/or to assist in crossing the aortic valve. Accordingly, multiple diagnostic procedures can be performed with the multi-functional catheter, such as a coronary angiogram and the trans-valvular pressure gradient measurement, while omitting reliance on additional catheters or a digital console system.

Furthermore, additionally or alternatively, the multi-functional catheter can include a multi-pressure channel arrangement. The multi-pressure channel arrangement can include one or more (e.g., three or more) pressure channels formed into the interior material of the central lumen or channel. The pressure channels can have elongated ellipse profiles, and can include three or more pressure channels terminating in side holes arranged in spiral around the catheter.

Additional advantages of the systems discussed herein will become apparent from the detailed description below.

FIG. 1 illustrates an example system 100 for performing cardiac diagnostic procedures using a multi-functional diagnostic catheter 102. The multi-functional diagnostic catheter 102 can include a catheter 104 (e.g., a primary body or outer sheath of the multi-functional diagnostic catheter 102) with one or more fluid pathways for measuring pressure, such as a multi-pressure channel arrangement 105 and/or a dual lumen arrangement 106 for performing a coronary angiogram, crossing an aortic valve, and measuring a trans-valvular gradient, as discussed in greater detail below.

In some examples, the dual lumen arrangement 106 includes a central lumen 108 disposed at least partly within the catheter 104, running a length of the catheter 104, and terminating at a first hub 110 to connect a first end hole 112 of the central lumen 108 to one or more pressure transducers 114. The first end hole 112 of the central lumen 108 can define an end hole of the catheter 104 at a distal end 116 of the catheter 104. The central lumen 108 can include a central tube or flexible pipe, such as a braided tube (as discussed in greater detail below regarding FIG. 3). The catheter 104 can also include an outer lumen 118 at least partly disposed within the catheter 104. The outer lumen 118 can be formed by an outer portion or outer tube 120 of the multi-functional diagnostic catheter 102 with one or more gaps or lumen channels 122 disposed at an inner surface of the outer tube 120. Additionally or alternatively, the outer lumen 118 can be formed of another internal tube running the length of the catheter 104 at least partially within the catheter 104 and adjacent to the central lumen 108. The outer lumen 118 can terminate at a second hub 124 (e.g., separate from the first hub 110) to connect the end hole of the outer lumen 118 (e.g., a second end hole 126 of the dual lumen arrangement 106) to the one or more pressure transducers 114. In some instances, the catheter 104 can be a French 6 catheter.

In some examples, the multi-functional diagnostic catheter 102 with the dual lumen arrangement 106 is operable to perform various diagnostic procedures on a heart 128 of a patient. For instance, the multi-functional diagnostic catheter 102 can include a welded tip 130 with a particular design that facilitates performing a coronary angiogram and crossing an aortic valve 132 without reliance on a second catheter, as discussed in greater detail below. Once the aortic valve 132 is crossed (e.g., as discussed in greater detail below regarding FIG. 5), the first end hole 112 of the central lumen 108 can be positioned in the left ventricular 134 with the second end hole 126 of the outer lumen 118 (e.g., the side hole) positioned in the aorta 136 above the aortic valve 132. In this trans-valvular position, a first pressure corresponding to the left ventricular 134 can be measured with the central lumen 108 and the first end hole 112 using the one or more pressure transducers 114; and a second pressure corresponding to the aorta 136 can be measured with the outer lumen 118 using the second end hole 126. As such, the multi-functional diagnostic catheter 102 can perform the coronary angiogram as well as a trans-valvular gradient measurement without requiring removal of the multi-functional diagnostic catheter 102 from the patient between these operations. Any of the functions or arrangements of the lumens discussed herein can be performed by or applied to the one or more pressure channels or pathways formed into an inner wall material of the central lumen 108, such as the interior material 710 the multi-pressure channel arrangement(s) 105 discussed below.

FIG. 2 illustrates an example system 200 for performing diagnostic procedures using the multi-functional diagnostic catheter 102, which can form at least a portion of the system 100 depicted in FIG. 1. FIG. 2 illustrates additional details of the first hub 110 and the second hub 124.

For instance, the first hub 110 can be a primary hub of the multi-functional diagnostic catheter 102 to connect the first end hole 112 at the distal end 116 to the one or more pressure transducers 114. The first hub 110 and the distal end 116 can define the length of the multi-functional diagnostic catheter 102. The central lumen 108 can be fully and/or at least partially contained within the multi-functional diagnostic catheter 102 between the distal end 116 and an end of the first hub 110 where the first hub 110 mates with the one or more pressure transducers 114. The second hub 124 can be a secondary hub that splits off or forks from the first hub 110 (e.g., the primary hub). A connector tube 202 can connect the second hub 124 to the first hub 110 and/or the catheter 104 to provide a fluidic pathway between the second hub 124 and the portion of the outer lumen 118 disposed within the catheter 104. Accordingly, the outer lumen 118 can have a first portion within the catheter 104 (e.g., at least between the second end hole 126 and a second hub juncture 204), and a second portion outside the catheter 104 formed by the connector tube 202. These components can collectively define the multi-functional diagnostic catheter 102.

FIG. 3 illustrates an example system 300 for performing diagnostic procedures using the multi-functional diagnostic catheter 102, which can form at least a portion of the system 100 depicted in FIG. 1. The system 300 depicted in FIG. 3 can include the welded tip 130 forming the distal end 116 of the multi-functional diagnostic catheter 102.

In some examples, the multi-functional diagnostic catheter 102 includes the central lumen 108 formed by an inner tube 302 and the outer lumen 118 formed between the inner tube 302 and the outer tube 120 (e.g., which forms the outer portion of the catheter 104). The welded tip 130 can be formed onto the inner tube 302 at the distal end 116 with a tip length 304 defined by the distal end 116. The distal end 116 of the multi-functional diagnostic catheter 102 can be a first end 306 of the welded tip 130, and the welded tip 130 can include a second end 308. The outer tube 120 can have a terminating exterior end 310 that mates with the second end 308 of the welded tip 130. In some instances, the outer tube 120 can have a first outer diameter 312 that corresponds with a second outer diameter 314 of the distal end 116 of the multi-functional diagnostic catheter 102 formed by the welded tip 130.

For instance, the first outer diameter 312 of the portion of the catheter 104 formed by the outer tube 120 can be the same or nearly the same as the second outer diameter 314 of the portion of the catheter 104 formed by the welded tip 130, such that the welded tip 130 forms a continuous and unchanging diameter of the catheter 104 to the distal end 116 (e.g., omitting any tapering features). The inner tube 302 forming the central lumen 108 can be constructed of a braided tube (e.g., metal, plastic, ceramic, composites thereof, and the like) and the outer tube 120 can be constructed of a non-braided tube (e.g., nylon, plastic, or other flexible material). The welded tip 130 can be welded to the inner tube 302 along the tip length 304 or at least a portion of the tip length 304, and/or the welded tip 130 can be welded or glued to the outer tube 120 with the second end 308 of the welded tip 130 mating with the terminating exterior end 310 of the outer tube 120. The transition from the flexible, non-braided outer tube 120 to the more rigid welded tip 130, along with the consistent, continuous diameter formed by the welded tip 130, can improve functionality of the multi-functional diagnostic catheter 102. This arrangement can enable the multi-functional diagnostic catheter 102 to be inserted or slid through the aortic valve 132 more easily than other catheters. Other catheters may have a tapered/narrowing end, or a flexible tip, making navigating the tip of other catheter to a desired location more difficult. In contrast, the multi-functional diagnostic catheter 102 can be inserted into the aorta 136, through the aortic valve 132 and into a desired position in the left ventricular 134 with ease (e.g., using a guidewire that is insertable and removable from the central lumen 108, as discussed below regarding FIG. 5). In other words, the welded tip 130 can be considered an expanded tip because it maintains the consistent diameter for the multi-functional diagnostic catheter 102 rather than tapering or narrowing the distal end 116 (e.g., even as the material changes from the flexible material of the outer tube 120 to the rigid material of the welded tip 130). Furthermore, as discussed in greater detail below regarding FIG. 8, the welded tip 130 can include an inner diameter that expands or is greater than the inner diameter of the central lumen 108 at other portions of the catheter 104.

In some instances, the multi-functional diagnostic catheter 102 can include one or more radiopaque markers 316 at various positions on the catheter 104 (e.g., barium sulfate, bismuth compounds, tungsten, platinum, and the like). The one or more radiopaque markers 316 can be at different particular locations with predefined spacing distances so that the one or more radiopaque markers 316 can be used to determine a location of the distal end 116 of the multi-functional diagnostic catheter 102 (e.g., including the first end hole 112 of the central lumen 108); a location of the welded tip 130 (e.g., the first end 306 and/or the second end 308 of the welded tip 130); a location of the second end hole 126 (e.g., side hole) of the outer lumen 118; and/or other locations or distances along the catheter 104 that may be useful to identify while navigating the multi-functional diagnostic catheter 102. For instance, the welded tip 130 can have a first radiopaque marker 318 at the distal end 116. The first radiopaque marker 318 can extend from the distal end 116 a first distance 320 along the welded tip 130 (which can be less than the tip length 304). The first radiopaque marker 318 can be used to identify a location of the distal end 116 when the multi-functional diagnostic catheter 102 is inserted into the patient.

Furthermore, the multi-functional diagnostic catheter 102 can include radiopaque markers 316 located on various portions of the outer tube 120. A second radiopaque marker 322 can be located at the terminating exterior end 310 of the outer tube 120. For instance, the second radiopaque marker 322 can extend from the terminating exterior end 310 a second distance 324 along the outer tube 120. The outer tube 120 can include a first gap between the second radiopaque marker 322 and a third radiopaque marker 326, the first gap being defined by a first separation distance 328. The third radiopaque marker 326 can be located proximate to the second end hole 126, and a second gap defined by a second separation distance 330 can separate the third radiopaque marker 326 from a fourth radiopaque marker 332. The fourth radiopaque marker 332 can be located proximate to the second end hole 126, for instance, opposite from the third radiopaque marker 326, such that the third radiopaque marker 326 and the fourth radiopaque marker 332 sandwich the second end hole 126. Additionally, the multi-functional diagnostic catheter 102 can include a welded tip gap defined by a welded tip gap distance 334 separating the first radiopaque marker 318 on the welded tip 130 from the second radiopaque marker 322.

In some examples, the arrangement of the different radiopaque markers 316 along with the various predefined distances between the radiopaque markers 316 improve the ability to track the distal end 116 and the location of the second end hole 126 as the multi-functional diagnostic catheter 102 is inserted into the patient and navigated to the various positions discussed herein. For instance, the radiopaque markers 316 and the predefined distances can be used to insert the multi-functional diagnostic catheter 102 into the aorta 136 to a desired location for performing an angiogram (e.g., injecting a contrast dye into the aorta 136). Moreover, the radiopaque markers 316 and the predefined distances can be used to navigate the distal end 116 through the aortic valve 132 and to a desired location in the left ventricular 134, while positioning the second end hole 126 at a desired location in the aortic valve 132, to perform the trans-valvular pressure gradient measurement and/or an angiogram of the left ventricular 134.

FIG. 4 illustrates an example system 400 for performing diagnostic procedures using the multi-functional diagnostic catheter 102, which can form at least a portion of the system 100 depicted in FIG. 1. The system 400 depicted in FIG. 4 can include the central lumen 108 and one or more outer lumen 118 to provide the dual lumen arrangement 106.

In some examples, the dual lumen arrangement 106 includes the central lumen 108 that defines the end hole at the distal end 116 of the multi-functional diagnostic catheter 102. The multi-functional diagnostic catheter 102 can also include the outer lumen 118 formed by the outer tube 120 of the multi-functional diagnostic catheter 102 with one or more gaps or lumen channels 122 disposed at an inner surface 402 of the outer tube 120. For instance, the one or more lumen channels 122 can be formed into the inner surface 402 and can extend a length of the catheter 104 from the one or more pressure transducers 114 to the second end hole 126 (e.g., and/or to the distal end 116). In some examples, the second end hole 126 is formed into the side of the multi-functional diagnostic catheter 102, and a blockage or stop 404 can be disposed proximate to the second end hole 126 (e.g., at a side of the second end hole 126 opposite from the one or more pressure transducers 114 and/or in a direction toward the distal end 116) so that the outer lumen can create a closed pressure system between the one or more pressure transducers 114 and the second end hole 126. In some examples, a plurality of lumen channels 122 can be formed into the inner surface 402 (e.g., substantially evenly spaced apart). Although only a single lumen channel 122 of the lumen channels 122 may be used to form the outer lumen 118, the other lumen channels 122 can provide a consistent, 360° flexibility for the multi-functional diagnostic catheter 102 so that the multi-functional diagnostic catheter 102 can reliably be movable in any direction as the multi-functional diagnostic catheter 102 is positioned for procedures. In some instances, the central lumen 108 has a first diameter that is greater than a second diameter of the outer lumen 118. The first diameter can be at least double the second diameter. Additionally or alternatively, the second diameter can be a distance between 5% and 50% of the second diameter.

FIG. 5 illustrates an example system 500 for performing diagnostic procedures using the multi-functional diagnostic catheter 102, which can form at least a portion of the system 100 depicted in FIG. 1. The system 500 depicted in FIG. 5 can include techniques for navigating the distal end 116 of the multi-functional diagnostic catheter 102 to one or more desired locations in the heart 128.

In some examples, the system 500 can include an aortic valve crossing procedure 502 for navigating the multi-functional diagnostic catheter 102 (e.g., the distal end 116 including the first end hole 112 of the central lumen 108) through the aortic valve 132 and into the left ventricular 134. The aortic valve crossing procedure 502 can be performed after an aortic diagnostic procedure. For instance, prior to crossing the aortic valve 132, the distal end 116 can be inserted into and positioned in the aorta 136. With the distal end 116 and/or the first end hole 112 positioned in the aorta 136, the aortic diagnostic procedure can be performed. The aortic diagnostic procedure can include injecting the contrasting dye into the aorta 136 via the central lumen 108 (e.g., a coronary angiogram). The aortic valve crossing procedure 502 can be performed after the aortic diagnostic procedure to move the distal end 116 from the aorta 136, through the aortic valve 132, and into the left ventricular 134 (e.g., using the radiopaque markers 316 to provide visualizations for guidance). In some examples, a guidewire 504 may be slid into the central lumen 108 via insertion into the first hub 110 (e.g., which can be disconnected from the one or more pressure transducers 114). The guidewire 504 can extend out of the distal end 116 and be pushed through the aortic valve 132, initially, such that the distal end 116 can be slid along the guidewire 504 to follow the guidewire 504 into the left ventricular 134. Once the distal end 116, including the first end hole 112 of the central lumen 108, is in the left ventricular 134, the guidewire 504 can be pulled back and/or retracted from the central lumen 108 and removed, or at least partially removed, from the multi-functional diagnostic catheter 102. In some instances, the guidewire 504 can be used to cross a stenotic aortic valve 132 and/or to cross an occlusion 506 in the aorta 136 and/or the aortic valve 132. The guidewire 504 is removable from the central lumen 108 while maintaining the central lumen 108 in the left ventricular 134 once the aortic valve 132 is crossed. Advantages can result from the ability to cross the aortic valve 132, the stenotic aortic valve 132, and/or the occlusion 506 using the same multi-functional diagnostic catheter 102 that is also used to perform the diagnostic procedures (e.g., rather than inserting a first catheter and/or steering system into the patient to perform the crossings, and then using another catheter to perform the different diagnostic procedures).

In some examples, a trans-valvular pressure gradient measurement can be generated using the first end hole 112 of the central lumen 108 in the left ventricular 134 to measure a first pressure value (e.g., a left ventricular pressure value); and the second end hole 126 of the outer tube 120 in the aortic valve 132 to measure a second pressure value (e.g., an aortic pressure value). Measuring the left ventricular pressure value and the aortic pressure value can include generating analog signals (e.g., two analog signals) with the one or more pressure transducers 114 (e.g., two pressure transducers 114) corresponding to these pressure values. Because the multi-functional diagnostic catheter 102 includes the dual lumen arrangement 106 and the one or more pressure transducers 114, no additional electronic systems, such as a digital-based console system, may be needed. As such, more complex digital-based pressure sensor console systems can be omitted, resulting in an easier and simpler process for performing the diagnostic procedures (e.g., with higher efficiency and lower costs).

Moreover, the dual lumen arrangement 106 (e.g., and other aspects of the multi-functional diagnostic catheter 102) can provide various diagnostic procedures in a variety of permutations and/or sequences. For instance, the aortic valve crossing procedure 502 can be performed before or after performing the coronary angiogram. The trans-valvular pressure measurement can be determined before or after performing the coronary angiogram. In some instances, a plurality of coronary angiograms can be performed and/or a plurality of trans-valvular pressure measurements can be calculated in various sequences (e.g., alternating between the different diagnostic procedures and/or multiple coronary angiograms followed by multiple trans-valvular pressure measurements, or combinations thereof).

FIG. 6 illustrates an example method 600 for performing diagnostic procedures using a multi-functional diagnostic catheter 102, which can be performed by the system 100 depicted in FIG. 1.

At operation 602, the method 600 can insert a multi-functional diagnostic catheter into an aorta of a patient, a central lumen of the multi-functional diagnostic catheter having a first end hole at a distal end of the multi-functional diagnostic catheter. At operation 604, the method 600 can make an initial crossing of an aortic valve with the distal end. At operation 606, the method 600 can measure a left ventricular pressure with the first end hole of the central lumen, the first end hole connecting to a pressure transducer via a first hub. At operation 608, the method 600 can measure an aortic pressure with a second end hole of an outer lumen disposed in the multi-functional diagnostic catheter, the outer lumen connecting to the transducer via a second hub. At operation 610, the method 600 can measure a trans-valvular pressure gradient based on simultaneous measurements of the left ventricular pressure and the aortic pressure (e.g., of operations 606 and 608). At operation 612, the method 600 can inject a contrast dye into the central lumen to perform a coronary angiogram.

It is to be understood that the specific order or hierarchy of steps in the method depicted in FIG. 6 and throughout this disclosure are instances of example approaches and can be rearranged while remaining within the disclosed subject matter. For instance, any of the operations depicted in FIG. 6 and throughout this disclosure can be omitted, repeated, performed in parallel, performed in a different order, and/or combined with any other of the operations depicted in FIG. 6. For instance, the method 600 can perform operation 612 before and/or after operations 604-610. Moreover, any of the systems or methods illustrated in FIGS. 1-6 can be combined together and/or form at least a portion of the system 100 depicted in FIG. 1.

FIGS. 7A and 7B illustrate an example system 700 which can be the same as or form at least a portion of the system 100 depicted in FIG. 1. The system 700 depicted in 7A and 7B includes a multi-functional diagnostic catheter 102 with the multi-pressure channel arrangement 105.

FIG. 7A depicts a 7 French (7Fr) catheter 702 including a cross-sectional view of a distal portion 704 at the distal end 116, and a cross-sectional view at a mid-shaft portion 706. The distal portion 704 can include a central lumen 108 having a distal portion inner diameter 708 of 0.067 in. and/or a distal portion outer diameter 709 of 0.093 in. At the mid-shaft portion 706, the catheter 104 can include the outer lumen channels 122 formed into the interior material 710, between the central lumen 108 and an outer surface 711 of the sidewall material forming the central lumen 108. These outer lumens or lumen channels 122 can have a curved elongated opening cross-sectional profile, such that the lumen channels 112 are curved elongated ellipse channels 712. Furthermore, the lumen channels 122 can have an angular dimension 714 of approximately 95° (e.g., 94.93°). Moreover, in some instances, the catheter 104 includes three lumen channels 122 terminating at three side openings 806, for instance at different distances, to form a staggered or spiral arrangement of side openings 806 around the outer surface 711 of the catheter 104.

Furthermore, some examples may include fewer than three or greater than three lumen channels 122 formed into the interior material (e.g., one, two, three, four, five six, seven, eight nine, ten, etc.) with a corresponding number of side openings 806). The lumen channels 122 can be evenly distributed and/or evenly spaced around the interior material 710.

In some instances, the distal portion 704 can have two or more side openings 806, which can improve pressure fidelity of the pressure transducer measurements. Portions of the catheter 104 with multiple lumens can have at least one side opening 806 drilled into each pressure lumen to improve pressure fidelity. The side openings 806 can wrap around the catheter 104 in a spiral fashion so that one or more of the side openings 806 are unobstructed by tissue and are able to freely transmit pressure. At the proximal portion of the catheter 104, the pressure lumens (e.g., the outer lumens 118 or lumen channels 122) can enter a common reservoir which is connected to the side pressure tubing (e.g., at the second hub 124).

Moreover, in some scenarios, the catheter 104 at the mid-shaft portion 706 can have a mid-shaft inner diameter 716 which is less than the distal portion inner diameter 708 of the distal portion 704. For instance, the mid-shaft inner diameter 716 can be 0.059 in. As such, the inner diameter of the central lumen 108 can transition from the mid-shaft inner diameter 716 to the distal portion inner diameter 708 at an inner diameter transition 804. Additionally or alternatively, the mid-shaft portion can have a same outer diameter 719 as the outer diameter 709 at the distal portion 704.

In some examples, as depicted in FIG. 7B, the system 700 includes a 6 French (6Fr) catheter 718 with a distal portion 720 (cross-sectional view) and a mid-shaft portion 722. The distal tip 720 can have a distal portion inner diameter 708 of 0.054 in.±0.002 in. and/or a distal portion outer diameter of 0.079 in.±0.002 in. Furthermore, the mid-shaft portion 722 can have the mid-shaft inner diameter 716 of 0.079 in.±0.002 in and the mid-shaft inner diameter 716 of 0.046 in.±0.002 in. As such, the outer diameter of the mid-shaft portion 722 can be greater than the outer diameter at the distal portion 720, and/or the inner diameter of the mid-shaft portion 722 can be less than the inner diameter at the distal portion 720. Additionally or alternatively, the 6Fr catheter 718 can include five lumen channels 122 (e.g., curved elongated ellipse channel 712) extending along the mid-shaft portion 722 and/or terminating at five side holes at a first end, and the second hub 124 at a second end. The 6Fr catheter 718 can include more or less lumen channels 122 than five in some instances.

FIG. 8 depicts an example system 800 which can be the same as or form at least a portion of the system 100 depicted in FIG. 1. The system 800 depicts a multi-functional diagnostic catheter 102 with the multi-pressure channel arrangement 105.

In some instances, a section 802 of the catheter 104 showing the inner diameter transition 804 of the mid-shaft inner diameter 716 of the mid-shaft portion 706 to the distal portion inner diameter 708 of the distal portion 704. Furthermore, the section 802 depicts the one or more side holes 806 at which the lumen channels 122 terminate. In some scenarios, such as those involving a plurality of lumen channels 122 extending along the mid-shaft portion 706, the side hole(s) 806 can be spaced a side hole distance 808 apart, such that the side holes form a staggered or spiraling arrangement 810 around the mid-shaft portion 706.

In some examples, the catheter 104 can include a distal tip 812. For instance, the distal portion 704 can extend a length 814 from the inner diameter transition 804 to a distal tip transition 816, at which point the distal portion inner diameter 708 can transition to a portion with a distal tip inner diameter 818 continuous with the distal portion inner diameter 708, maintaining the expanded diameter to the end hole 112. Accordingly, sliding friction of the guidewire 504 can be reduced by the configuration of inner lumen diameters increasing and creating additional sliding space for the guidewire 504. The distal tip 812 can be a soft material (e.g., silicon, rubber, mesh, and so forth) at the catheter 104 to prevent tissue injury by attaching to the expanded tip.

FIG. 9 depicts an example system 900 including the catheter 104 performing various cardiac procedures 902 and methods, which can be performed by any of the systems 100-800 disclosed herein.

In some instances, at operation 904 the catheter 104 can be positioned with the distal end 116 in the aorta 136, and the guide wire 504 (e.g., a straight guidewire 504) can be inserted through the central lumen 108 out the distal end 116. At operation 906, the heart entry procedure 902 can include extending the guidewire 504 out the distal end 116 and through the aortic valve 132 into the left ventricular 134. The guidewire 504 may pass through the mid-shaft inner diameter 716 to the wider distal portion inner diameter 708 of the central lumen 108 before exiting the distal tip 116 and probing/crossing the aortic valve 132. At operation 908, the heart entry procedure 902 can include extending the catheter 104 through the aortic valve 132 using the guidewire 504 by sliding the outer lumen 118 over the guidewire 504. The guidewire 504 can remain with its guidewire tip 907 in the left ventricular 134 until the distal end 116 of the catheter 104 has passed through the aortic valve 132 (e.g., an occluded aortic valve 132) and drawn the guidewire 504 at least partially or fully back into the central lumen 108. Operation 908 can also include moving the distal end 116 of the catheter 104 through the aortic valve 132 until the first end hole 112 and/or one or more side holes 806 are positioned in the left ventricular 134 while retracting the guidewire 504 into the central lumen 108. Furthermore, the cardiac procedure 902 can include withdrawing or extracting the guidewire 504 from the central lumen 108 while the catheter 104 remains positioned across the left ventricular

134. Additionally or alternatively, the cardiac procedure 902 can include performing one or more heart entry, diagnostic procedures and/or treatment procedures using the central lumen 108 and/or the lumen channels 122, with the side holes 806 and/or end hole 112 positioned in the aorta 136 and/or left ventricular 134 (e.g., a cross-aortic pressure measurement, an angiogram procedure, or so forth).

In some scenarios, smooth wire transit provides important tactile feedback to the operator to allow him/her to safely advance across the diseased aortic valve. The catheter shapes disclosed herein can be optimized to cross the aortic valve, including diseased aortic valve. Furthermore, the catheter 104 can be multi-functional by performing multiple operations of housing the guidewire while positioning the guidewire in the aorta 136, using the guidewire to cross the aortic valve 132, provide the central lumen 108 for retracting the guidewire 504 from the left ventricular 134 and/or the patient, and take aortic pressure measurements on both sides of the aortic valve 132 simultaneously. As such, disruption or trauma caused to the patient by using two separate insertions for a guidewire a separate catheter (e.g., inserting and extracting the guidewire before inserting the catheter) is reduced. Furthermore, the systems disclosed herein use pressure opening fluidly coupled to the pressure transducers at the hub to determine the pressure values, thus omitting sensors along the catheter 104 and omitting an electronic console, which reduces bulkiness, complexity, and costs, by improving operational efficiency.

While the present disclosure has been described with reference to various implementations, it will be understood that these implementations are illustrative and that the scope of the present disclosure is not limited to them. Many variations, modifications, additions, and improvements are possible. More generally, implementations in accordance with the present disclosure have been described in the context of particular implementations. Functionality may be separated or combined differently in various implementations of the disclosure or described with different terminology. These and other variations, modifications, additions, and improvements may fall within the scope of the disclosure as defined in the claims that follow.

What is claimed is:

1. A multi-functional diagnostic catheter comprising:
   a catheter with a pressure measurement arrangement operable to perform a coronary angiogram, cross an aortic valve, and measure a trans-valvular gradient, the pressure measurement arrangement including:
      a central pressure measurement pathway formed by a central tube disposed at least partly within the catheter, the central pressure measurement pathway terminating at a first hub to connect an end hole of the central pressure measurement pathway to a pressure transducer, and
      an outer pressure measurement pathway formed by an outer tube surrounding the central tube, the outer pressure measurement pathway having a first portion disposed within the catheter and a second portion disposed outside the catheter, the second portion terminating at a second hub to connect a side hole of the outer pressure measurement pathway to the pressure transducer, the side hole being located at a side of the catheter spaced a defined distance from an end of the catheter.

2. The multi-functional diagnostic catheter of claim 1, wherein, the outer pressure measurement pathway is a pressure channel disposed in an interior material forming the central pressure measurement pathway.

3. The multi-functional diagnostic catheter of claim 2, wherein,
   a distal tip has a first inner diameter greater than an inner diameter of the central pressure measurement pathway.

4. The multi-functional diagnostic catheter of claim 3, wherein,
   the distal tip is formed of a soft material.

5. The multi-functional diagnostic catheter of claim 4, wherein,
   the defined distance is a first defined distance, and
   the catheter includes a first radiopaque marker at the end hole of the central pressure measurement pathway and a second radiopaque marker circumferentially around the side of the catheter a second defined distance from the first radiopaque marker.

6. The multi-functional diagnostic catheter of claim 1, wherein,
   the pressure measurement arrangement is operable to measure a left ventricular pressure using the end hole of the central pressure measurement pathway while measuring an aortic pressure using the side hole of the outer pressure measurement pathway.

7. The multi-functional diagnostic catheter of claim 6, wherein,
   measuring the left ventricular pressure and the aortic pressure uses two analog signals generated by two pressure transducers while omitting reliance on a digital-based pressure sensor console system.

8. The multi-functional diagnostic catheter of claim 1, wherein,
   the central pressure measurement pathway is operable to receive a guidewire for crossing an aortic valve, and
   the guidewire is removable from the central pressure measurement pathway while maintaining the central pressure measurement pathway in a left ventricular once the aortic valve is crossed.

9. The multi-functional diagnostic catheter of claim 1, wherein,
   the central pressure measurement pathway is operable to inject a contrast dye prior to crossing an aortic valve to perform selective coronary angiogram.

10. The multi-functional diagnostic catheter of claim 1, wherein,
   a first portion of the multi-functional diagnostic catheter, including the central pressure measurement pathway with the outer pressure measurement pathway, has a first inner diameter; and
   a second portion of the multi-functional diagnostic catheter, including the central pressure measurement pathway and omitting the outer pressure measurement pathway, has a second inner diameter greater than the first inner diameter.

11. A multi-functional diagnostic catheter comprising:
   a catheter with a multi-pressure channel arrangement operable to perform a coronary angiogram, cross an aortic valve, and measure a trans-valvular gradient, the multi-pressure channel arrangement including:
      a central pressure measurement pathway formed by a central tube disposed at least partly within the catheter, the central pressure measurement pathway terminating at a first hub to connect a distal end hole of the central pressure measurement pathway to one or more pressure transducers; and one or more outer pressure measurement pathways formed by an outer tube surrounding the central tube and a sidewall material of the central pressure measurement pathway, the one or more outer pressure measurement pathways terminating at a second hub to connect one or more side holes of the one or more outer pressure measurement pathways to the one or more pressure transducers, the one or more side holes being located at a side of the catheter spaced one or more defined distances from an end of the catheter.

12. The multi-functional diagnostic catheter of claim 11, wherein, the one or more side holes include at least three side holes in a staggered arrangement around the catheter.

13. The multi-functional diagnostic catheter of claim 12, wherein, the one or more outer pressure measurement pathways includes at least three elongated ellipse channels.

14. The multi-functional diagnostic catheter of claim 13, wherein, the multi-functional diagnostic catheter is a 7 French (7Fr) catheter or a 6 French (6Fr) catheter.

15. The multi-functional diagnostic catheter of claim 11, further comprising:

a first inner diameter at a mid-shaft portion of the multi-functional diagnostic catheter which extends from a proximal portion of the multi-functional diagnostic catheter to a near-distal portion of the multi-functional diagnostic catheter; and a second inner diameter at a distal portion of the multi-functional diagnostic catheter, the second inner diameter being greater than the first inner diameter.

16. The multi-functional diagnostic catheter of claim 11, wherein, the central pressure measurement pathway is operable to cross a stenotic aortic valve using a guidewire disposed within the central pressure measurement pathway; and the multi-functional diagnostic catheter is operable to measure a left ventricular pressure using the distal end hole of the central pressure measurement pathway while measuring an aortic pressure using the one or more side holes of the one or more outer pressure measurement pathways upon crossing the stenotic aortic valve with the guidewire.

17. A method to perform multiple diagnostic functions using a catheter with a multi-pressure measurement pathway arrangement, the method comprising:

measuring a left ventricular pressure with an end hole of a central pressure measurement pathway, the central pressure measurement pathway formed by a central tube being at least partly disposed within the catheter and terminating at a first hub to connect the end hole of the central pressure measurement pathway to a pressure transducer, the end hole of the central pressure measurement pathway being located at a distal end of the catheter; and measuring an aortic pressure with one or more end holes of one or more outer pressure measurement pathway, the one or more outer pressure measurement pathway formed by an outer tube surrounding the central tube and disposed in the catheter, the one or more outer pressure measurement pathway terminating at a second hub to connect one or more end holes of the one or more outer pressure measurement pathway to a pressure transducer, the one or more end holes being located along an outer sidewall of the catheter spaced one or more defined distances from the end hole of the central pressure measurement pathway.

18. The method of claim 17, wherein, measuring the left ventricular pressure and the aortic pressure is performed with three or more side holes to measure a trans-valvular gradient while omitting reliance on a pressure sensor console system.

19. The method of claim 17, further comprising:

making an initial crossing of an aortic valve with the central pressure measurement pathway using a guidewire disposed within the central pressure measurement pathway.

20. The method of claim 17, further comprising:

injecting a contrast dye into coronary arteries using the central pressure measurement pathway before or after measuring a trans-valvular gradient with the central pressure measurement pathway and three or more outer pressure measurement pathway.

* * * * *